United States Patent [19]
Voll et al.

[11] Patent Number: 5,062,309
[45] Date of Patent: Nov. 5, 1991

[54] DEVICE FOR TAKING SAMPLES OF BOTTOM SEDIMENTS FROM WATER BASINS

[75] Inventors: Martin A. Voll; Robert K. Eiskop, both of Tallin, U.S.S.R.

[73] Assignee: Institut Khimii Akademii Nauk Estonskoi SSR, Tallinn, U.S.S.R.

[21] Appl. No.: 528,343

[22] Filed: May 25, 1990

Related U.S. Application Data

[63] Continuation-in-part of Ser. No. 404,076, Sep. 7, 1989, abandoned.

[51] Int. Cl.⁵ .............................................. G01N 1/04
[52] U.S. Cl. ................................................. 73/864.44
[58] Field of Search ........... 73/864.44, 864.45, 864.63, 73/864.65; 175/403, 405, 58

[56] References Cited

U.S. PATENT DOCUMENTS 4,709,584 12/1987 Voll et al. ......................... 73/864.44

FOREIGN PATENT DOCUMENTS 1543043 10/1968 France ............................... 73/864.44
623128 7/1978 U.S.S.R. .
0842453 6/1981 U.S.S.R. ........................... 73/864.65
1013810 4/1983 U.S.S.R. .
1100522 6/1984 U.S.S.R. ........................... 73/864.44

Primary Examiner—Robert Raevis
Attorney, Agent, or Firm—Fleit, Jacobson, Cohn, Price, Holman & Stern

[57] ABSTRACT

A device for taking samples of bottom sediments from water basins includes at least one vertical sectional coring tube having a closed upper end provided with a check valve. The device includes, in the form of a cover, also a device for preventing the loss of a taken sample in the process of the device lifting, closing in a rest position the open lower end of the coring tube and being connected with the movable rod. The rod is secured by hinges to the carrying element. The upper end of the coring tube is secured to the carrying element.

5 Claims, 2 Drawing Sheets

DEVICE FOR TAKING SAMPLES OF BOTTOM SEDIMENTS FROM WATER BASINS

This application is a continuation-in-part of application Ser. No. 07/404,076, filed Sept. 7, 1989, and now abandoned.

FIELD OF THE INVENTION

The invention relates to the oceanographic instruments for investigating properties of substances and, more particularly, to devices for taking samples of bottom sediments from water basins.

BACKGROUND OF THE INVENTION

Known in the prior art is a device for taking samples of bottom sediments from water basins, comprising a vertical coring tube with a closed upper end provided with a check valve, a ballast weight on the upper end of the coring tube and the side stationary supports (cf. USSR Inventor's Certificate No. 1,013,810, class G01N, 1/10, published in 1983).

However, under the conditions of rough water in water basins such a device fails to provide a guaranteed sampling as water masses in the volume of a wave move upwards at a speed greater than that of the device proper, because of which the check valve in the upper end of the coring tube gets opened and the taken sample is partially or even completely lost. Under the conventional conditions the sample is retained in the coring tube due to the fact that with the device being lifted, the check valve is closed and the reduced pressure is built up in the space between the closed upper end of the coring tube and the sample contained therein.

Also known in the prior art is a device for taking samples of bottom sediments from water basins, comprising a vertical coring tube with a closed upper end provided with a check valve and a means for preventing the loss of a taken sample in the process of the device lifting (cf. USSR Inventor's Certificate No. 623,128, class G01N, 1/04, published in 1978).

In the known device the coring tube is made in the form of two concentrically installed tubes, the internal tube being intended for filling with a taken sample. As to a means for preventing the loss of a taken sample, a valve is used. The valve is installed at the cutting shoe and is made in the form of two flaps closing under the action of the springs. Before the device sinking onto the bottom of a water basin the flaps are cocked. The device sinks in the soil under the action of the weight thereof. The column of the soil, moving upwards in the cavity of the tube, completely opens the valve flaps, releasing them from the cocking stop, and fills the internal tube. While lifting the device the valve flaps close under the action of the springs and the weight of the taken sample. The known device prevents the loss of a taken sample in the process of lifting. However, the natural structure of bottom sediment layers is disturbed. This results from the following. The valve flaps are, prior to sampling, in a half-open position and open completely only under the action of the force developed by the column of the sample moving upwards. The weak layers (especially the surface layer) are not able to stand the force needed for the complete opening of the flaps, in the zone of the valve flaps the section for the sample passing is decreased and as a result, the compression and intermixing of the sample takes place, leading to the disturbance of the initial structure of the sample layers.

The invention is aimed at providing a device for taking samples of bottom sediments from water basins with a means for preventing the loss of a taken sample in the process of the device lifting of such a design which will ensure an undisturbed natural structure of the bottom sediment layers in the taken sample.

SUMMARY OF THE INVENTION

It is an object of the invention to improve the representativeness of the taken samples.

It is another object of the invention to improve the representativeness of the taken samples under adverse weather conditions.

The nature of the invention consists in that in a device for taking samples of bottom sediments from water basins, comprising a vertical coring tube with a closed upper end provided with a check valve and a means for preventing the loss of a taken sample in the process of the device lifting, according to the invention, the means for preventing the loss of a taken sample is made in the form of a cover, secured to a movable forked rod. The forked rod has two upper ends and one lower end and the length exceeding the length of the coring tube. The upper part of the rod is branched in the form of two branches, having said upper ends of the rod, the lower part is unbranched, having said lower end of the rod. The upper ends of the branches are secured by means of the hinges to the carrying element, to which by means of its upper end also the coring tube is secured. The upper ends of the branches are secured symmetrically relative to the coring tube and with the distance from each other exceeding the diameter of the coring tube. The cover is secured by means of the hinges to the branches at the places being before the place where the branched part of the rod goes over to the unbranched one, so that in a rest position the cover closes the lower end of the coring tube. In a rest position the lower end of the rod is below the level of the lower end of the coring tube and has a plate, secured therewith by means of a hinge. To enable us to take parallel samples, the device may comprise more than one coring tube.

The cover may suitably be made in the form of a plate with a perpendicular semicircular bead suiting the external surface of the coring tube from the place of the securing of the cover to the rod.

It is desirable to bend the unbranched part of the rod relative to the branched one with an angle $\alpha < 180°$ in the plane of displacement of the rod with the cover while opening the lower end of the coring tube.

It is advisable to supply the branches of the rod with the locks, secured by means of the rods to the branches above the places where the cover is secured so that in a rest position the locks catch the coring tube.

It is also adviable that the device for taking samples of bottom sediments should be provided with at least three supports having upper and lower ends and the length exceeding the length of the coring tube, placed uniformly around the coring tube and secured by their upper ends to the carrying element.

A device for taking samples of bottom sediments from water basins made according to the present invention makes it possible to take representative samples of bottom sediments even under adverse weather conditions (in case of rough water and craft motions), when the speed of upward movement of water masses exceeds the lifting speed of the device with a taken sample. In the case of disappearance of the reduced pressure in the upper part of the coring tube, the taken sample of bottom sediments is reliably held by the cover, which closes the lower end of the coring tube. The device ensures an undisturbed natural structure of bottom sediment layers in a taken sample.

BRIEF DESCRIPTION OF THE DRAWINGS

The invention will now be described in greater detail with reference to specific embodiments thereof, taken in conjunction with the accompanying drawings, wherein.

DETAILED DESCRIPTION OF THE INVENTION

Figure 1:
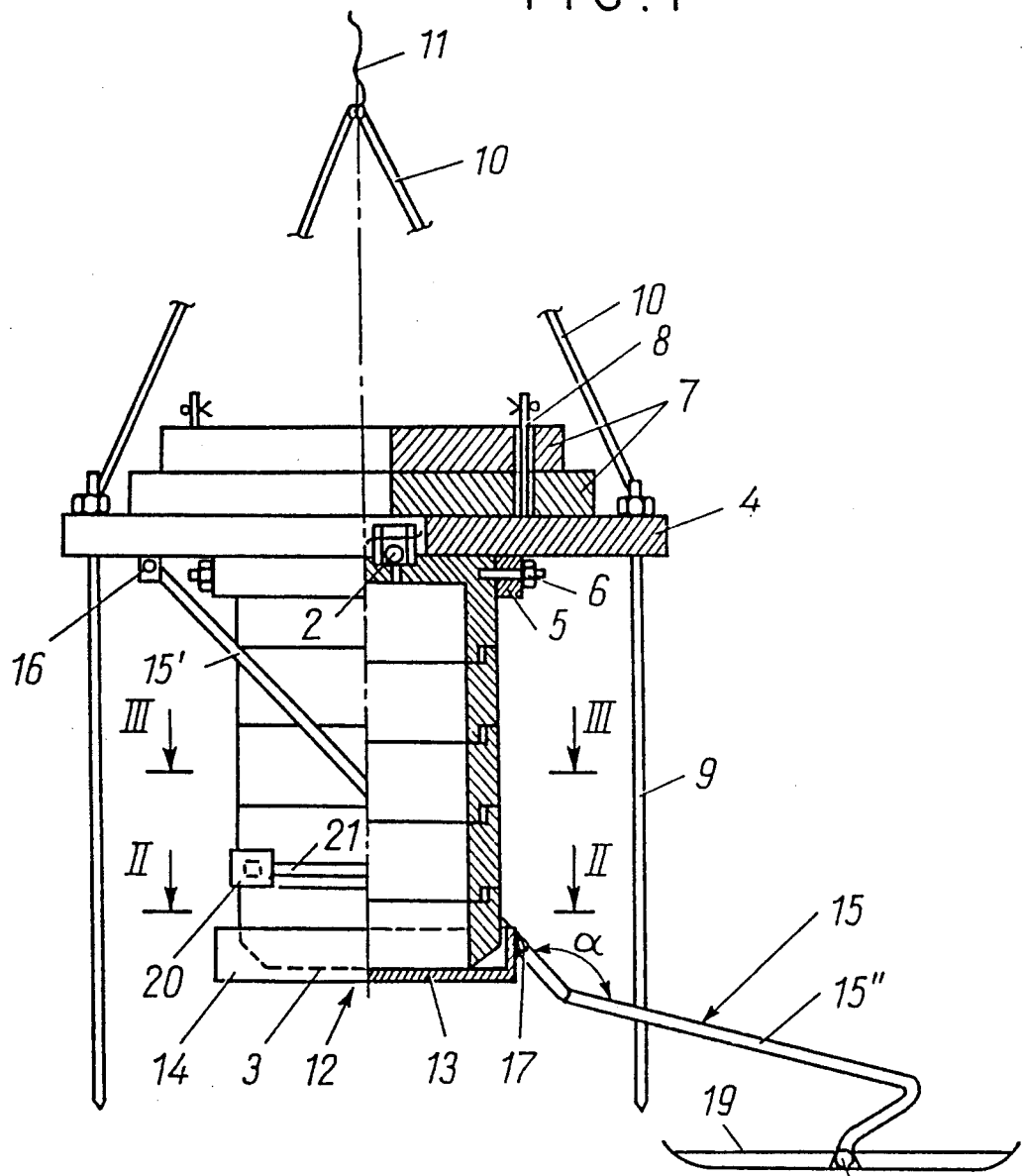
FIG. 1 is a general view, partly in section, illustrating a device for taking samples of bottom sediments from water basins.
Figure 2:
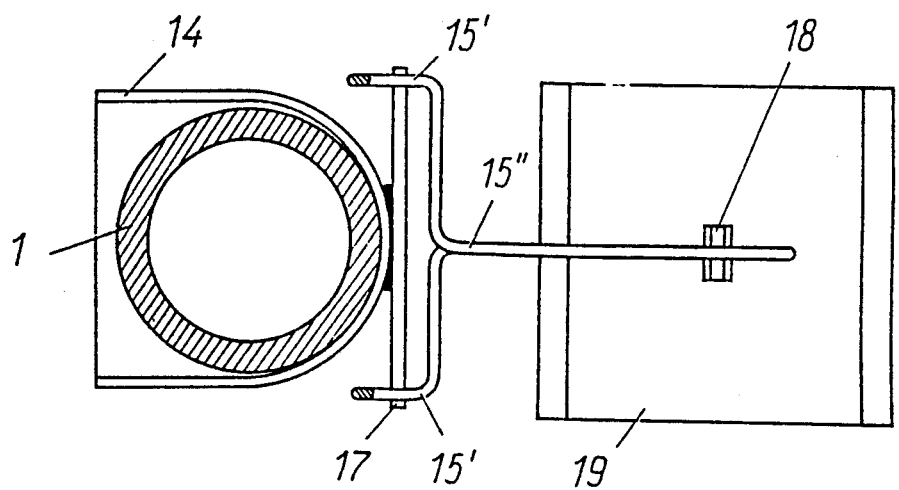
FIG. 2 is a section taken on line II—II of FIG. 1.
Figure 3:
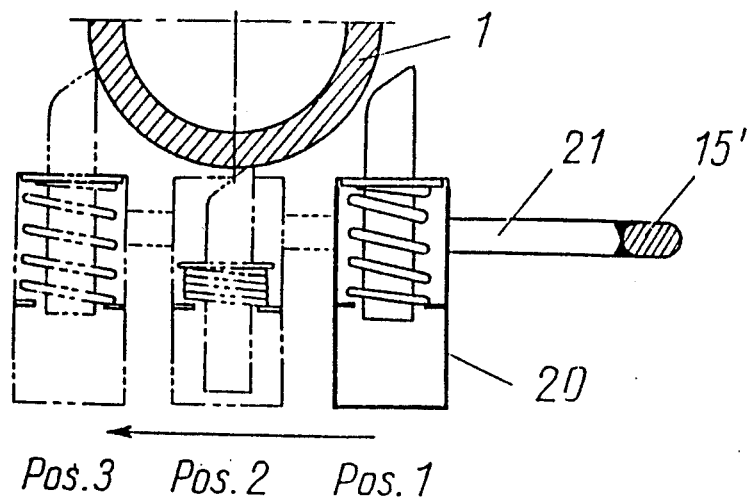
FIG. 3 is a section taken on line III—III of FIG. 1.

A device for taking samples of bottom sediments from water basins, illustrated in FIGS. 1, 2 and 3, comprises a vertical sectional coring tube 1 with a closed upper end in which a check valve 2 is built and an open lower end 3, a carrying element 4, being at the same time the main ballast weight, to which by means of a strip 5 and the bolts 6 the coring tube 1 by its upper end is secured, an additional ballast weight 7 consisting of a set of removable disks installed on the uprights 8, the supports 9, at least three in quantity, having the length exceeding the length of the coring tube 1, placed uniformly around the tube 1 and secured by their upper ends to the carrying element 4, the bars 10 by means of which the device is suspended to a rope 11. As a means for preventing the loss of a taken sample in the process of the device lifting the device comprises a cover 12, made in the form of a plate 13 with a perpendicular semicircular bead 14. The cover 12 is secured to the forked rod 15, which has a branched upper part with two branches 15', having two upper ends of the rod 15, and an unbranched lower part 15", having the lower end of the rod 15. The branches 15' are secured by their upper ends to the carrying element 4 by means of the hinges 16 symmetrically relative to the coring tube 1 and with the distance from each other exceeding the diameter of the coring tube 1. The cover 12 is secured by means of the hinges 17 to the branches 15' at the places guaranteeing that in a rest position the plate 13 of the cover 12 fits closely the lower end 3 of the coring tube 1. To the lower end of the rod 15 by means of a hinge 18 a plate 19 is secured. The unbranched part 15" of the rod 15 is bent relative to the branched part 15' with an angle α < 180°. Locks 20 may optionally be used to catch the coring tube during ascent. If used, the locks 20 are made, for example, in the form of spring-loaded tongues and are secured to the branches 15' by means of the rods 21 above the hinges 17 so that in a rest position, with the cover 12 closing the ends of tube 11, locks 20 catch the coring tube 1; this position is shown in FIG. 1 and is position 3 of FIG. 3.

The device for taking samples of bottom sediments from water basins operates in the following manner.

Figure 4:
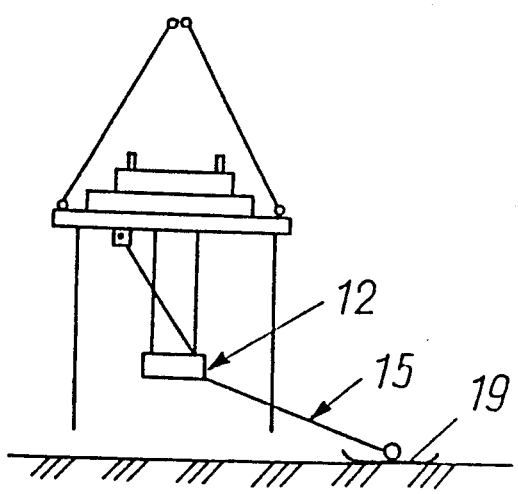
FIG. 4 diagrammatically illustrates a device at the moment when the plate comes in contact with the bottom of a water basin in the process of the device sinking.
Figure 5:
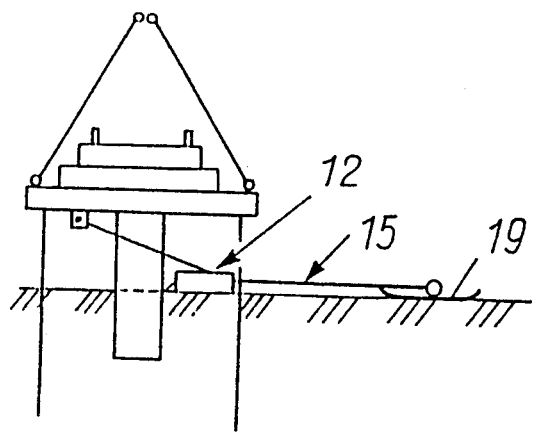
FIG. 5 is the same of FIG. 4 at the moment of taking a sample.

In a rest position the cover 12 closes the lower end 3 of the coring tube 1 (FIG. 4). While sinking the device to the bottom of a water basin, the position of the cover 12 depends on the speed of sinking, the weights of the cover 12, the rod 15 and the plate 19. Before coming in contact with the bottom, the inclined position of the rod 15 assists in the sliding of the plate 19 along the bottom of the water basin. At the same time, together with the rod 15 moves also the cover 12 connected with it and the lower end 3 of the coring tube 1 begins to open and opens completely during further device sinking. The supports 9 prevent the device from tipping. Now the sampling takes place (FIG. 5). After the sample is taken, the device is lifted by means of the rope 11. The check valve 2 in the upper end of the coring tube 1 gets closed. A reduced pressure is built up between the upper end of the coring tube 1 and the column of the sample due to which the taken sample is retained in the coring tube 1. While the device lifting, the closing of the lower end 3 of the coring tube 1 with the cover 12 starts, contributing to the action of the weights of the rod 15, the cover 12 and the plate 19, the latter being additionally acted upon by the dynamic pressure of water column. From the moment when the plate 19 is pulled off from the bottom of the water basin the plate 13 of the cover 12 fits closely the lower end 3 of the coring tube 1, closing it completely.

The invention as used and described with reference to FIGS. 4 and 5 is without the optional locks 20 being present in the structure. If locks 20 are used and present in the structure, the locks 20 are initially in position 1 as shown in FIG. 3, and thereby do not interfere with the function of the structure during descent and sample taking. While closing the cover 12 during ascent, the locks 20 catch the coring tube 1 and close up (FIG. 3) by moving from position 1, through position 2, and into position 3. This ensures no loss of the taken sample even in case of rough water in the water basin. The locked position 3 is also illustrated in FIG. 1.

The invention has been described in detail with particular reference to preferred embodiments thereof, but it will be understood that variations and modifications can be effected within the spirit and scope of the invention.

What is claimed is:

1. A device for taking samples of bottom sediments from water basins, said device comprising:
   at least one vertical coring tube;
   sections of said coring tube arranged in succession one after another longitudinally of said tube;
   a closed upper end of said tube;
   a check valve built in said upper end;
   an open lower end of said tube;
   a carrying element, said upper end of said tube being secured to said carrying element;
   a forked rod having a branched upper end and an unbranched lower end and the entire length exceeding the entire length of said tube;
   said branched upper part of said rod having two branches with upper ends of said rod;
   said unbranched lower part of said rod having a lower end of said rod;
   said branches of said branched part, pivotally secured by said upper ends to said carrying element symmetrically relative to said tube and with the distance from each other exceeding the diameter of said tube;
   a cover, pivotally secured to said branches at the places guaranteeing that in a rest position said cover closes said lower end of said tube;
   said lower end of said rod, being in a rest position below the level of said lower end of said tube;

a plate, pivotally secured to said lower end of said rod.

2. A device according to claim 1, wherein said cover is made in the form of a plate with a perpendicular border edge being semi-circular from the place where said cover is secured to said rod and suiting the external surface of the coring tube.

3. A device according to claim 1, wherein said unbranched part of said rod is bent relative to said branched part with an angle $\alpha < 180°$ in the plane passing the vertical axis of said tube and being transverse to the plane of said branched part.

4. A device according to claim 1, wherein said branches of said branched part of said rod are supplied with locks secured by means of rods to said branches above the places where said cover is secured, so that in a rest position said locks catch said coring tube.

5. A device according to claim 1, which includes at least three supports, having upper and lower ends and the length exceeding the length of said coring tube placed uniformly around said tube and secured by said upper ends to said carrying element.

* * * * *